United States Patent
Pavlovsky

(10) Patent No.: US 7,782,462 B2
(45) Date of Patent: Aug. 24, 2010

(54) SONO-PHOTONIC GAS SENSOR

(75) Inventor: Igor Pavlovsky, Cedar Park, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 218 days.

(21) Appl. No.: 11/945,610

(22) Filed: Nov. 27, 2007

(65) Prior Publication Data
US 2008/0212100 A1   Sep. 4, 2008

(51) Int. Cl.
*G01N 21/00* (2006.01)
(52) U.S. Cl. .................. 356/437; 356/436
(58) Field of Classification Search .......... 356/432–444
See application file for complete search history.

(56) References Cited

U.S. PATENT DOCUMENTS

| | | |
|---|---|---|
| 4,157,470 A | 6/1979 | Kotaka et al. |
| 4,251,727 A | 2/1981 | Piercy |
| 4,322,621 A | 3/1982 | Aagard |
| 4,370,553 A | 1/1983 | Waycaster et al. |
| 4,500,207 A | 2/1985 | Maiden |
| 4,557,603 A | 12/1985 | Oeher |
| 4,633,714 A * | 1/1987 | Mazumder et al. ............ 73/596 |
| 4,678,914 A | 7/1987 | Melrose et al. |
| 4,708,941 A | 11/1987 | Giuliani |
| 4,726,225 A | 2/1988 | Brace |
| 4,907,166 A | 3/1990 | Corenman et al. |
| 5,026,992 A | 6/1991 | Wong |
| 5,129,401 A | 7/1992 | Corenman et al. |
| 5,173,749 A | 12/1992 | Tell et al. |
| 5,221,871 A | 6/1993 | Fuchs et al. |
| 5,235,235 A | 8/1993 | Martin et al. |
| 5,251,482 A | 10/1993 | Bates et al. |
| 5,289,715 A | 3/1994 | Stapes et al. |
| 5,325,704 A | 7/1994 | Mariani et al. |
| 5,464,982 A | 11/1995 | Drucker et al. |
| 5,468,961 A | 11/1995 | Gradon et al. |
| 5,571,944 A | 11/1996 | Pfeifer et al. |
| 5,585,635 A | 12/1996 | Graham |
| 5,644,085 A | 7/1997 | Lorraine et al. |
| 5,693,945 A | 12/1997 | Akiyama et al. |
| 5,742,200 A | 4/1998 | He |
| 5,753,797 A | 5/1998 | Forster |
| 5,793,295 A | 8/1998 | Goldstein |
| 5,801,297 A | 9/1998 | Mifsud et al. |
| 5,817,922 A | 10/1998 | Rapp et al. |
| 5,876,674 A | 3/1999 | Dosoretz et al. |
| 5,880,552 A | 3/1999 | McGill et al. |
| 5,918,257 A | 6/1999 | Milfsud et al. |
| 5,970,803 A | 10/1999 | Staples et al. |

(Continued)

OTHER PUBLICATIONS

International Search Report and Written Opinion mailed May 22, 2008; Application No. PCT/US2007/085582, 12 pages.

*Primary Examiner*—Michael P Stafira
(74) *Attorney, Agent, or Firm*—Kelly Kordzik

(57) ABSTRACT

Sensing a gas includes introducing a gas into a chamber, forming a standing acoustic wave in the chamber, and irradiating the chamber with electromagnetic radiation. Some of the electromagnetic radiation passes into the chamber, through the standing acoustic wave in the chamber, and out of the chamber. An amount of electromagnetic radiation that passes out of the chamber, or is transmitted through the chamber, is detected. A concentration of the gas in the chamber can be assessed.

6 Claims, 2 Drawing Sheets

U.S. PATENT DOCUMENTS

| | | |
|---|---|---|
| 6,006,585 A | 12/1999 | Forster |
| 6,008,928 A | 12/1999 | Sachse et al. |
| 6,016,203 A | 1/2000 | Martin |
| 6,029,500 A | 2/2000 | Tom |
| 6,044,332 A | 3/2000 | Korsah et al. |
| 6,067,840 A | 5/2000 | Chelvayohan et al. |
| 6,190,035 B1 | 2/2001 | Smith |
| 6,194,735 B1 | 2/2001 | Martin |
| 6,236,951 B1 | 5/2001 | Payne et al. |
| 6,338,272 B1 | 1/2002 | Heuft et al. |
| 6,354,160 B1 | 3/2002 | Staples et al. |
| 6,359,278 B1 | 3/2002 | Graham |
| 6,422,061 B1 | 7/2002 | Sunshine et al. |
| 6,429,019 B1 | 8/2002 | Goldstein et al. |
| 6,437,326 B1 | 8/2002 | Yamate et al. |
| 6,538,728 B1 | 3/2003 | Stolle et al. |
| 6,649,416 B1 | 11/2003 | Kauer et al. |
| 6,662,627 B2 * | 12/2003 | Arnott et al. ............... 73/24.02 |
| 6,819,811 B1 | 11/2004 | Goldstein |
| 6,843,102 B1 | 1/2005 | Shulga et al. |
| 6,939,717 B2 | 9/2005 | Jiang et al. |
| 6,989,549 B2 | 1/2006 | Diekmann et al. |
| 7,047,792 B1 | 5/2006 | Bhethanabotla et al. |
| 7,047,793 B2 | 5/2006 | Lee et al. |
| 7,091,869 B2 | 8/2006 | Forster et al. |

* cited by examiner

SONO-PHOTONIC GAS SENSOR

CROSS-REFERENCE TO RELATED APPLICATIONS

This application claims the benefit under 35 U.S.C. §119 (e)(1) of U.S. provisional application 60/867,364 filed on Nov. 27, 2006, which is incorporated by reference herein in its entirety.

TECHNICAL FIELD

This invention relates to gas sensing by spectroscopic methods, and more particularly to assessment of gas concentration in the presence of signals induced by a standing acoustic wave in a measurement chamber.

BACKGROUND

There are many technologies based on the measurement of absorption of electromagnetic radiation in gases. These technologies typically include an infrared light source, a gas-filled measurement cell with two optical windows, and a means to detect the absorption signal. This means can be acoustic (for instance, a microphone in photoacoustic spectroscopy), optical (for instance, a photodetector), etc.

Optical absorption in a gas is known to be a function of its absorption cross-section $\alpha$, gas concentration c, and optical path length x. Given the intensity of incident light $I_0$ and the intensity of the light past the absorption volume I, then, according to Beer's law, $I/I_0 = \exp(-\alpha c x)$. For $SF_6$ gas with $\alpha = 4 \times 10^{-17}$ cm$^2$/molecule, c=100 ppm ($2.7 \times 10^{15}$ molecules/cm$^3$), and x=3 cm, $\alpha c x = 0.362$, and the value of $I/I_0$ is 0.696. A difference of this magnitude between the intensity of the incident light and the intensity of the light past the absorption volume can be easily detected with a single measurement cell (that is, without a reference cell). For gases with smaller absorption cross-sections and/or concentrations, however, a typical change in the intensity of the measured light is on the order of $10^{-3}$–$10^{-6}$ of the intensity of the incident beam. For this purpose, a second, reference cell is used for comparison of two optical signals. With this differential design, all the components of the sensor must have very stable parameters to detect changes in the optical signal on the order of one part per million.

DESCRIPTION OF DRAWINGS

Like reference symbols in the various drawings, indicate like elements.

DETAILED DESCRIPTION

Absorption of electromagnetic radiation by a gas in a chamber is a function of the gas concentration of the absorbing gas, which can be one of several components in the chamber, and other variables. Consequently, the absorption also depends on the gas pressure in the chamber. When an acoustic standing wave is created in the chamber, then the corresponding gas pressure oscillations can be measured by a detector, and gas concentration can be assessed without the use of a reference cell.

Figure 1:
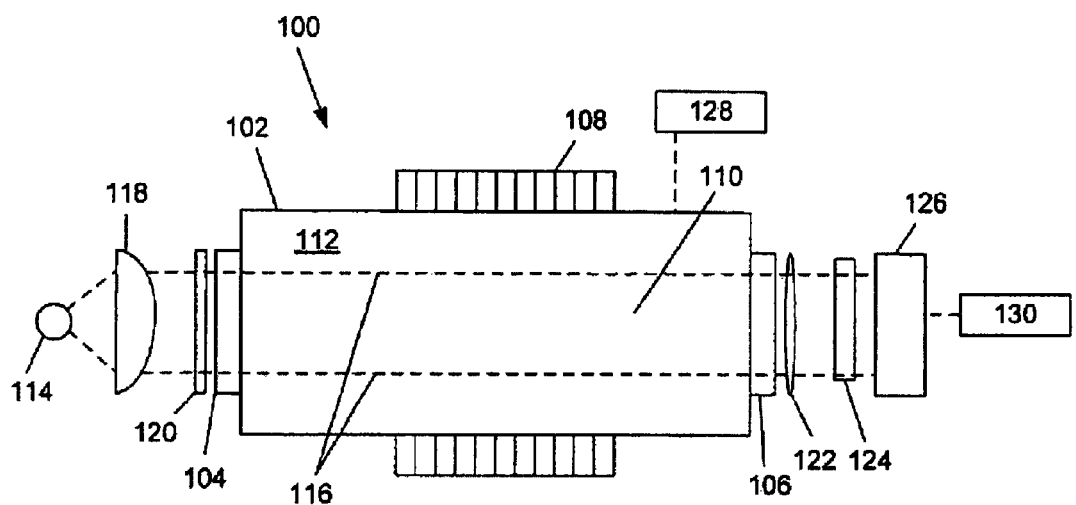
FIG. 1 is a schematic diagram of a device for sensing a gas.

FIG. 1 depicts a schematic diagram of a gas sensor 100. In some embodiments, chamber 102 is a cell with a known volume. In other embodiments, chamber 102 is open, such that gas flow through the chamber is unrestricted. For example, for high sound frequencies, during a short period of time between pressure oscillations, the viscosity of the gas is sufficient to inhibit the gas inside the chamber from reaching equilibrium with the gas outside the chamber. Thus, restriction of gas flow is not required.

A cross section of the chamber 102 can be, for example, round or rectangular. The chamber 102 can include windows 104, 106. One or more acoustic transducers 108 are coupled to the chamber 102, and are operable to form a standing acoustic wave 110 in the gas 112 contained in the chamber 102. Electromagnetic radiation source 114 is coupled to the chamber 102 such that gas 112 in the chamber can be irradiated with electromagnetic radiation 116 from the electromagnetic radiation source. The electromagnetic radiation source 114 can be one or more single wavelength, narrow linewidth, or broadband sources, or any combination thereof. The electromagnetic radiation source 114 can emit infrared, visible, or ultraviolet radiation, or any combination thereof.

Electromagnetic radiation 116 passes from source 114 through one or more lenses 118 and/or filters 120, into the chamber 102 through the window 104, through the chamber, out of the chamber through the window 106, and through optional lenses 122 and/or filters 124 to detector 126. Detector 126 is, for example, one or more photodetectors capable of detecting infrared, visible, or ultraviolet radiation, or any combination thereof. The amount of radiation that passes out of the chamber or is transmitted through the chamber is indicative of the amount of radiation absorbed by the gas in the chamber. Detector 126 detects a variation or change in the optical radiation induced by the standing acoustic wave.

Absorption (or transmission) can be measured at one or more wavelengths by the detector 126. In some implementations, filters 124 are interference filters chosen for sequential or parallel beam splitting at the chamber optical output. Sequential beam splitting can be realized using semi-transparent or dichroic mirrors, and parallel beam splitting can be used if a beam falls onto a mosaic filter with detectors behind each filter. The latter method can be advantageous for sensing at two or four different wavelengths.

Figure 2:
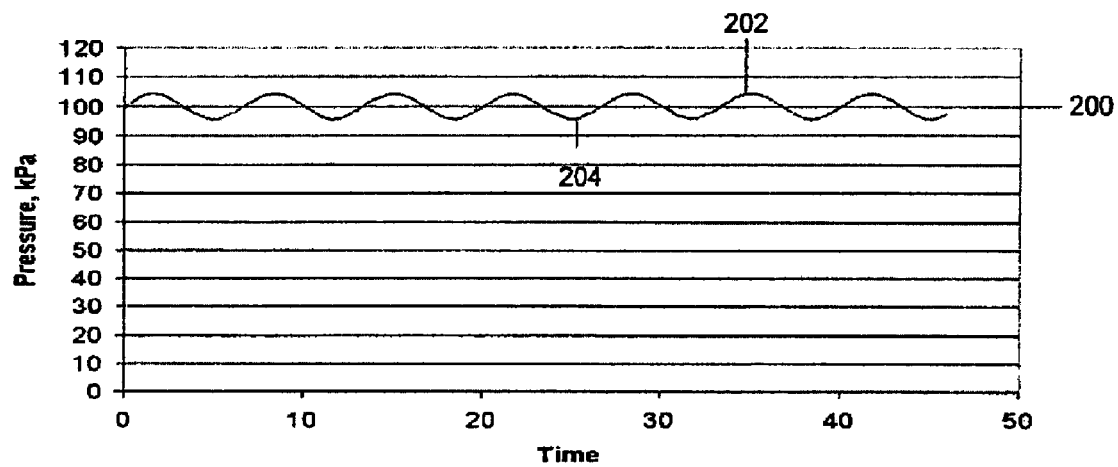
FIG. 2 depicts standing wave acoustic oscillations in a chamber.

In one embodiment, a piezoelectric transducer (output 100 dB at 100 cm) coupled to a chamber with a width of 5 cm creates a standing sound wave at a frequency f=3000 Hz, with a sound intensity equal to about a 2 Pa pressure wave. In the center of the chamber, at 2.5 cm from the transducer, the pressure is about (100 cm/2.5 cm)×2 Pa=80 Pa. With two similar transducers placed against each other, the pressure in the chamber is about 160 Pa. For an acoustic chamber with a resonance at the transducer's oscillation frequency and a cell quality factor Q~25, the sound pressure created is about 4 kPa. Transducers with 120 dB output produce pressure $p_a$ of about 40 kPa inside the resonant acoustic chamber. The total pressure in the chamber as a function of time is $$p(t) = p_0 + p_a \sin(2\pi f t),$$

where $p_0$ is the average pressure, or ambient atmospheric pressure. For transducers with 120 dB output, $p_0$=100 kPa. The normalized pressure variation is $$1 + (p_a/p_0)\sin(2\pi f t),$$

and the harmonic component in this signal has an amplitude of $(p_a/p_0)$=4% of the total signal, as shown in FIG. 2, where $p_0$ 200 is an average of $p_{max}$ 202 and $p_{min}$ 204.

Thus, in the presence of a standing wave, the pressure in the chamber and optical signal (radiation that passes out of the chamber or transmitted radiation detected by the detector) oscillate about a mean value that corresponds to the absence of the standing wave. The difference in optical signal for two pressures, $p_{max}$ and $p_{min}$, is proportional to the concentration of the absorbing gas, which may be one of several components in the chamber. A concentration of a gas in a chamber can be assessed by measuring optical signal, or difference in optical signal, for two pressures, as well as $p_0$. The optical signal as a function of time in the presence of a standing wave yields the difference in optical signal $\Delta I$, as well as $I_0$, needed to assess the concentration of the gas in the chamber.

For low absorption signals, $$I/I_0 \sim 1 - \alpha cx, \text{ or } \Delta I/I_0 \sim \alpha cx.$$

Since the absorption coefficient directly depends on the gas concentration or pressure, this can be rewritten as $$\Delta I/I_0 \sim \alpha c_0 x (1 + (p_a/p_0)\sin(2\pi ft)),$$

where $c_0$ is the gas concentration at the atmospheric pressure, $p_0$. For $SF_6$ with concentrations of 100 ppm and 1 ppm, the change in the absorption signal due to the presence of the standing sound wave in the chamber will be $1.2 \times 10^{-2}$ and $1.45 \times 10^{-4}$ of the incident light intensity, respectively. Thus, a variation in the amount of absorbed radiation induced by the standing wave is detected as a variation in radiation transmitted through the chamber.

For an optical source including a broad band incandescent IR radiation source with emissivity of 0.9 and power of 1 W, heated to the temperature of 600° C., with a light collection efficiency of a collimator of 0.3, and an optical filter at 10 microns with 3% FWHM bandpass and 60% transmission at maximum wavelength, the output power is about 1.38 mW. In this case, the optical radiation oscillation at the output of such an acoustic chamber with the described source is about $2 \times 10^{-7}$ W for 100 ppm $SF_6$. This power can be detected by a variety of optical sensors, including pyroelectric detectors, which are sensitive to oscillations of the radiation at a frequency of 0.1 Hz to 10 kHz rather than constant power radiation. Typical responsivity of a pyroelectric detector is $5 \times 10^5$ volt/watt, and the noise equivalent power (NEP) is about $2 \times 10^{-10}$ W at 1 kHz radiation modulation frequency. With this detector, signal-to-noise ratio of the described sensor can be about 1000:1, giving a detection limit of about 100 ppb $SF_6$.

Figure 3:
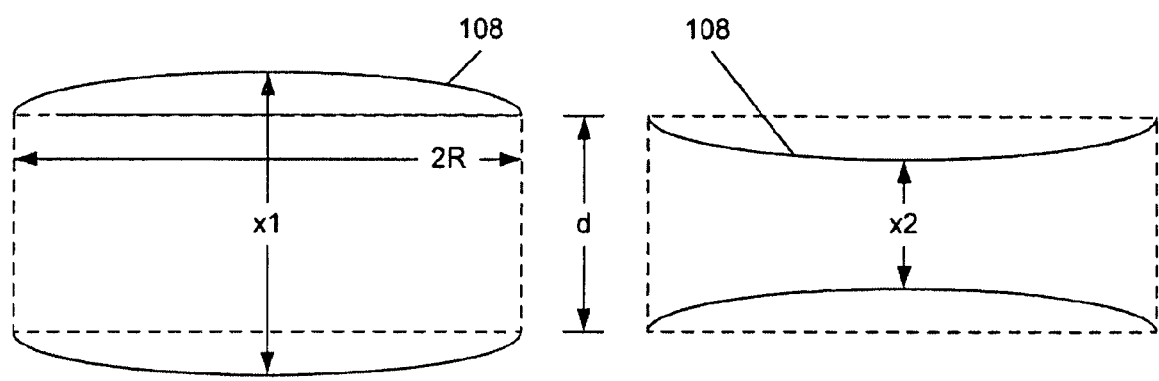
FIG. 3 is a schematic diagram of round transducers for use with an acoustic chamber.

In some implementations, the gas sensing device is compact, such that a distance between the transducers is less than the length of the first acoustic longitudinal mode. For round transducers, the pressure deviations depend on geometrical characteristics of the chamber and the volume displacement by the transducers. FIG. 3 depicts a side view of round transducers 108 that can be coupled to an acoustic chamber, for instance, to each base of a cylindrical chamber. For transducer radius R, the transducer displacement $x = (x1-x2)/2$, and the volume displacement (two round transducers) $V_t = 2 \times (\pi x/6)(3R^2 + x^2)$. For a chamber with height d, the chamber volume $V_c = \pi d R^2$. In this case, the pressure variation can be calculated as $$\Delta P/P = 1/(1-V_t/V_c) - 1/(1+V_t/V_c),$$

For small volume variations, the pressure variation can be calculated as $$\Delta P/P = 2V_t/V_c = (x/d)(1+x^2/3R^2).$$

The sensitivity of the gas sensing devices described herein can be increased by adjusting one or more various parameters, alone or in combination. For example, in some embodiments, the power of the optical source can be increased. Using a 10 W infrared source will increase the sensitivity of the sensor by a factor of about 10. The output of the transducers can be increased in some embodiments. For example, increasing the output of the transducers by 20 dB will result in an increase in sensitivity by a factor of about 10. Increasing the path length of the chamber can also increase the sensitivity of the gas sensing device. For example, using a multi-pass chamber can increase the sensitivity by an order of magnitude. Increasing the chamber pressure by, for example, a gas pump 128 (depicted in FIG. 1), can increase the sensitivity by a factor of about 2-5. Increasing the sensitivity of a gas sensing device can also be achieved by, for example, using detector with less noise and/or a digital signal processor 130 (depicted in FIG. 1) for signal analysis. Implementation of a selected combination of these improvements will allow the detection of $SF_6$ in air at concentrations on the order of parts per trillion. Other gases with lower absorption cross-sections can be detected at concentrations on the order of parts per billion.

A number of embodiments of the invention have been described. Nevertheless, it will be understood that various modifications may be made without departing from the spirit and scope of the invention. Accordingly, other embodiments are within the scope of the following claims.

What is claimed is:

1. A method of sensing a gas, the method comprising the steps of:
    introducing the gas into a chamber;
    forming pressure variations in the chamber with piezoelectric acoustic transducers, wherein a distance between the transducers is less than a diameter of the transducers and shorter than a first longitudinal acoustic mode of the chamber;
    irradiating the chamber with electromagnetic radiation, such that some of the electromagnetic radiation passes into the chamber, through the pressure variations in the chamber, and out of the chamber; and
    detecting an amount of electromagnetic radiation that passes out of the chamber.

2. The method of claim 1, wherein the electromagnetic radiation comprises infrared radiation.

3. The method of claim 1, wherein the electromagnetic radiation comprises visible radiation.

4. The method of claim 1, wherein the step of detecting an amount of electromagnetic radiation that passes out of the chamber comprises assessing an amount of electromagnetic radiation transmitted through the chamber.

5. The method of claim 4, further comprising the step of assessing an amount of electromagnetic radiation of more than one wavelength transmitted through the chamber.

6. The method of claim 1, further comprising the step of assessing a concentration of the gas in the chamber.

* * * * *